United States Patent [19]

Feaster

[11] Patent Number: 4,629,462
[45] Date of Patent: Dec. 16, 1986

[54] INTRAOCULAR LENS WITH COILED HAPTICS

[76] Inventor: Fred T. Feaster, 800 8th Ave., Suite 234, Fort Worth, Tex. 76104

[21] Appl. No.: 630,879

[22] Filed: Jul. 13, 1984

[51] Int. Cl.$^4$ ............................................. A61F 2/16
[52] U.S. Cl. ........................................................ 623/6
[58] Field of Search ............................ 3/13, 1; 623/6

[56] References Cited

U.S. PATENT DOCUMENTS

| 4,249,271 | 2/1981 | Poler | 3/13 |
| 4,418,431 | 12/1983 | Feaster | 3/13 |
| 4,442,553 | 4/1984 | Hessburg | 623/6 |
| 4,446,581 | 5/1984 | Blake | 3/13 |

FOREIGN PATENT DOCUMENTS 2111835 7/1983 United Kingdom ...................... 3/13

OTHER PUBLICATIONS

"Use of the Intraocular Lens in the Aphakic Eye, part 1: The Anterior Chamber Intraocular Lens" by Philip C. Hessburg, Henry Ford Hosp. Med. Journal, vol. 28, No. 1, 1980, pp. 71-75.

Posterior Chamber Lens-Control-Loop Haptic-Ultra C-Loop Model C304 (2 page advertisement) Ioptex Intraocular Lenses, 1301 Optical Drive, Azusa, CA 91702, Jun. 1983.

Primary Examiner—Ronald L. Frinks
Attorney, Agent, or Firm—Arthur F. Zobal

[57] ABSTRACT

The intraocular lens may have closed loop haptics or open loop haptics. Each closed loop haptic has two coil portions and each open loop haptic has one coil portion. The purpose of the coil portions is to provide the desired flexibility and to provide for geometric stable haptic flexion upon the application of compression force to the peripheral portions of the haptics towards the lens body.

26 Claims, 21 Drawing Figures

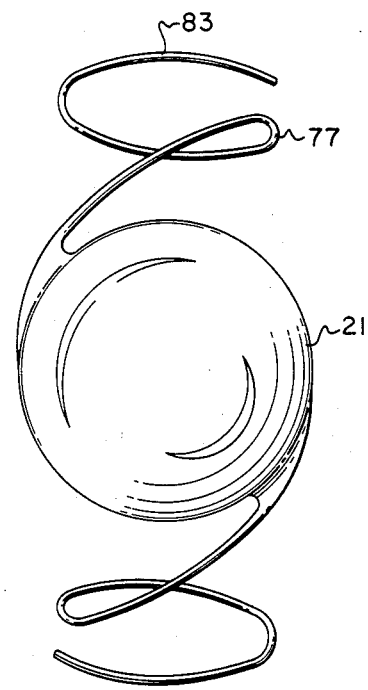
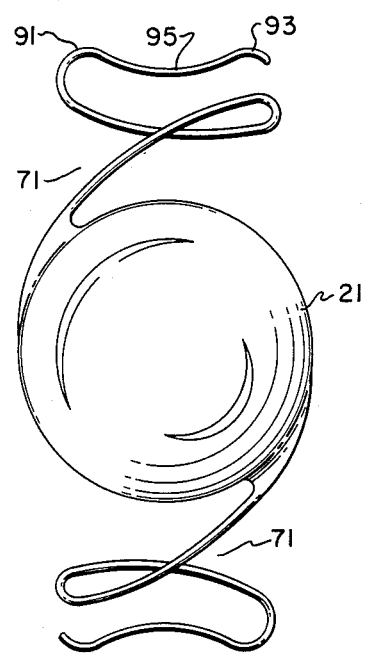
Fig. 14
Fig. 15
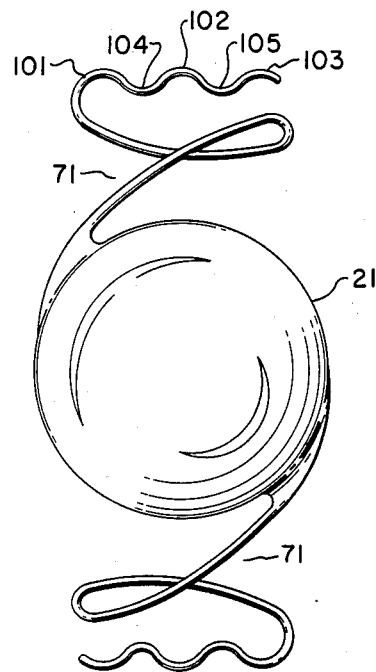
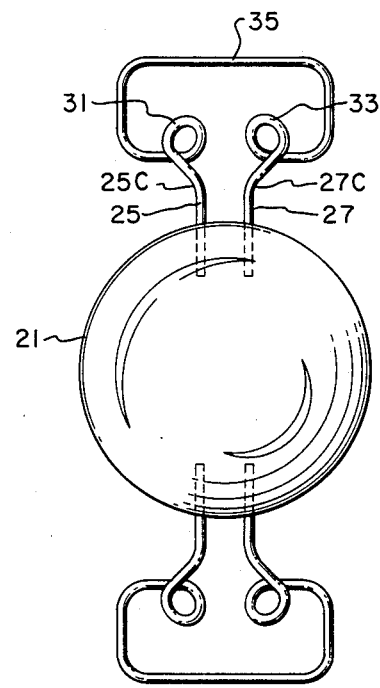
Fig. 16
Fig. 17

INTRAOCULAR LENS WITH COILED HAPTICS

BACKGROUND OF THE INVENTION

1. Field of the Invention

The invention relates to an intraocular lens for use as an artificial lens implant in the human eye.

2. Description of the Prior Art

The following U.S. patents disclose intraocular lens which employ different types of open loop or closed loop haptics or position fixation members: U.S. Pat. Nos. 4,010,496, 4,085,467, 4,159,546, 4,174,543, 4,242,760, 4,244,060, 4,251,887, 4,253,200, 4,280,232, 4,285,072, 4,298,994, 4,298,995, 4,304,012, 4,316,292, 4,328,595, 4,338,687, 4,340,979, 4,361,913, 4,370,760, 4,377,873, 4,418,431. The purpose of the haptics or position fixation members is to hold or support the optic or lens body in the eye in a stable position with respect to the pupil and visual axis. As pointed out in U.S. Pat. No. 4,418,431, a certain degree of flexibility of the haptics is desirable. In addition, a desirable feature of any intraocular lens is that it exhibits geometrically stable haptic flexion which consists of three basic properties: (1) no side to side movement of the haptic when it flexes; (2) no change in the location or amount of touch of the haptic with the tissue of the eye; (3) the haptic must be able to flex without movement of the optic forward, backward, or side ways when in the anterior or posterior chambers of the eye (uniplanar loop flexion). Very few of the known intraocular lenses have all of these properties. Previously, it had been thought that flexion of closed loop haptics owuld invariably result in anterior optic movement (movement of the optic forward) when placed in the anterior chamber of the eye. This is particularly true for lenses which are made in an angulated or vaulted design in order to support the lens away from the iris. Such anterior optic movement is undesirable since it may result in engagement of the optic with the cornea on its posterior surface which can result in damage to the cornea.

SUMMARY OF THE INVENTION

It is an object of the invention to provide a new and useful intraocular lens having unique types of open loop and closed loop haptics or position fixation members which have a desirable amount of flexibility and geometrically stable haptic flexion.

The haptics or position fixation members have coiled or curled flexible portions which tend to unwind (open) or wind (close) when the haptics flex upon compression of the haptics toward the optic. This has particular advantage when employed in closed loop type haptics in that it provides considerable flexibility and prevents or minimizes anterior optic movement thereby providing uniplanar flexion allowing the lens to be safely used in the anterior chamber of the eye. It also allows for the necessary flexibility required for either anterior or posterior chamber inplantation of intraocular lenses having either closed loop or open loop haptics. By employing coiled flexible portions in open loop haptics, additional locations of flexibility are provided.

The intraocular lens of the invention comprises a lens body or optic having a haptic or position fixation member which comprises a stem portion connected to the optic or lens body, a coiled portion, and a peripheral portion adapted to engage the tissue of the eye. In the embodiment disclosed, the closed loop haptics, have two coiled portions and the open loop haptics, have one coiled portion.

More specifically, the closed loop haptics, have two stems with a coiled portion connected between each stem and its peripheral portion. The open loop haptics, have a single stem with a coiled portion coupled between the stem in its peripheral portion which has a free end. In the open loop haptics, an elbow is located between the coiled portion and the peripheral portion thereof.

BRIEF DESCRIPTION OF THE DRAWINGS

In FIGS. 2 and 3, the lenses are of a convex-planar shape. In FIGS. 4 and 5, the lenses are of a biconvex shape. In FIGS. 3 and 5, the haptics are angulated or vaulted.

FIG. 14 is an intraocular lens having two open loop haptics similar to that of FIG. 14 but having curved stems.

FIG. 15 is an intraocular lens having two open loop haptics each of which has one coil. The peripheral portions of each of the haptics are shaped to provide two rounded fixation portions whereby four point fixation is provided for the lens overall.

FIG. 16 is an intraocular lens having two open loop haptics each of which has one coil. The peripheral portions of each of the haptics are shaped to provide three rounded fixation portions whereby six point fixation is provided totally for the lens overall.

FIG. 17 is an intraocular lens having two closed loop haptics similar to that of FIG. 1 but with diverging stems.

DESCRIPTION OF THE PREFERRED EMBODIMENTS

Figure 1:
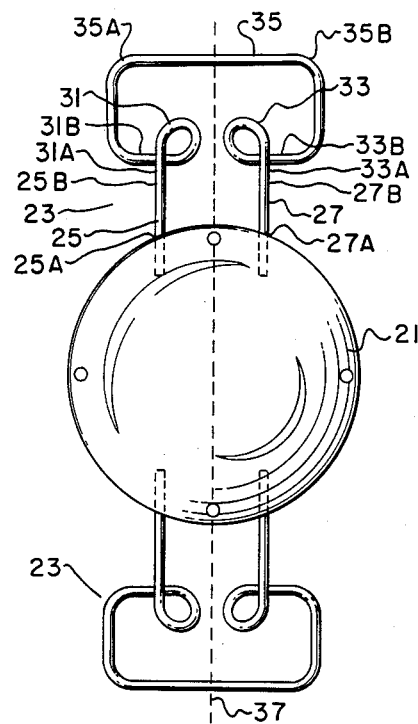
FIG. 1 is a top plan view of an intraocular lens of the invention which has two closed loop haptics each having two coiled portions.
Figure 6:
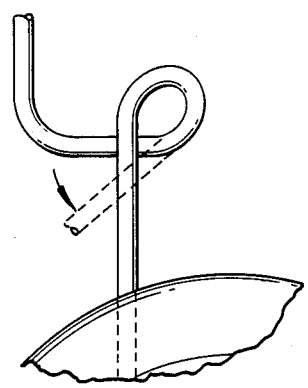
FIG. 6 illustrates the manner in which one of the coils of one of the haptics of the lens of FIG. 1 unwinds when pressure is applied to the peripheral portion of the haptic toward the lens body.
Figure 7:
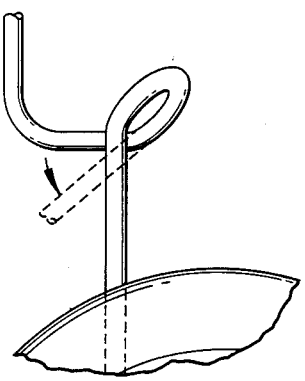
FIG. 7 is a view similar to that of FIG. 6 but with the loop of the coil being more oval shaped.
Figure 9:
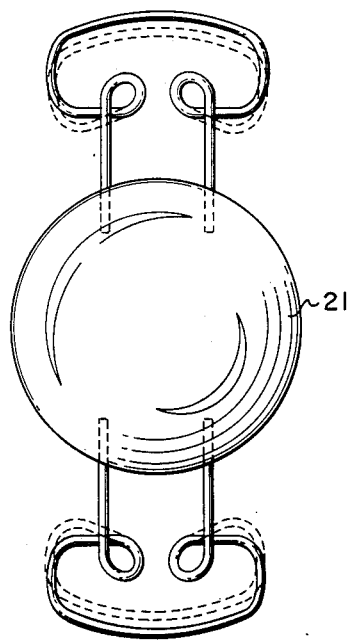
FIG. 9 illustrates movement of the peripheral portions and unwinding of the coils of the haptics when pressure is applied to the peripheral portions of the haptics toward the lens body.

Referring to FIG. 1, the intraocular lens comprises a circular, transparent central or medial lens body or optic 21. Extending outward from opposite sides of the periphery lens body 21 are two closed loop haptics or position fixation members 23. The two members 23 are identical. Each member 23 comprises two stems or proximal portions 25 and 27 having ends 25A and 27A joined proximally to the lens body 21. The other ends 25B and 27B of the stems 25 and 27 are formed into coils or curls 31 and 33 having ends 31A, 31B and 33A, 33B which cross each other. The ends 31B and 33B of the coils 31 and 33 extend or/are connected to a peripheral or seating portion 35 adapted to seat against or engage the tissue of the eye. The stems 25 and 27 and coils 31 and 33 are located at equidistant points respectively from a plane 37 coinciding with and passing through the axis of the optic 21 and which bisects the peripheral portions 35. Each peripheral portion 35 has two fixation portions 35A and 35B whereby there is four point fixation totally for the lens overall. The lens of FIG. 1 preferrably will be used in the anterior chamber of the eye. The coils 31 and 33 provide the desired amount of flexibility and result in geometrically stable haptic flexion. Of particular importance is that the coils 31 and 33 prevent or minimize anterior optic movement (movement of the optic toward the cornea) upon flexion of the members 23 upon the application of pressure to the fixation points 35A and 35B of the members 23 toward the lens body 21. The coil portions 31B and 33B act as lever arms to provide flexibility when compression forces are applied to each of the members 23 in directions to shorten the member 23. This lever-like action causes the coils 31 and 33 to unwind, open up or enlarge in their diameters yielding to the force of compression causing the "lever arms" to move in arc like paths towards the optic 21 as illustrated in FIGS. 6, 7 and 9. The coils or curls 31 and 33 are formed by each of the loop members 23 passing under itself as seen in FIG. 1 as it loops progressing from the optic 21 toward the outer loop or peripheral portion 35. That is, the loop member 23 begins from its fixed positions 25A and 27B at the optic 21, progresses outwardly, begins its curls, completes the curls by passing under itself (as seen in FIG. 1) to then progress further to the outer portion 35 of the loop. By passing under itself in this fashion without attachment, each lever arm of each loop member 23 is free to follow its arcuate path toward the optic without touching the inner portion of the loop member which might impede or inhabit its movement. The two coils or curls 31 and 33 of each member 23 provide an equal and symmetrical amount of loop flexibility.

Figure 2:
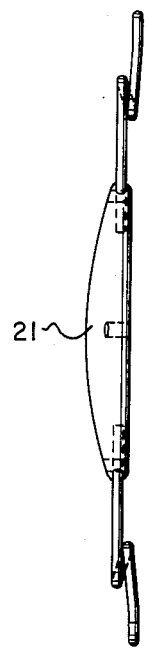
FIGS. 2–5 are side views of intraocular lenses of the invention having two closed loop haptics.
Figure 3:
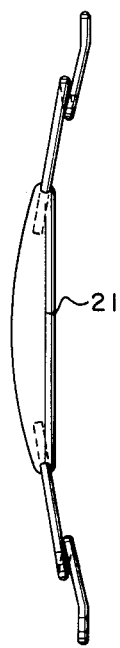
Figure 4:
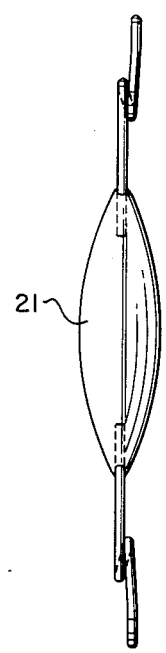
Figure 5:
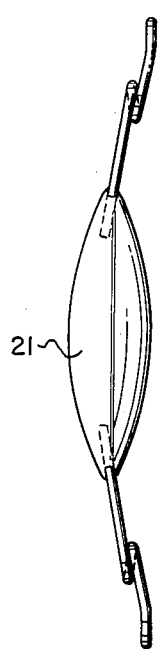

The lens body 21 and the loop members 23 in one embodiment can be made separately from suitable plastic. In this embodiment, the members 23 can be attached to the lens body 21 by drilling suitable holes into the peripheral edge of the member 21; inserting the free ends of the stems 25 and 27 into the holes and bonding the stems 25 and 27 to the lens body by suitable heat treatment. The lens body 21 may be formed in a convex-planar shape as shown in FIGS. 2 and 3, in a biconvex shape as shown in FIGS. 4 and 5 or in other configurations. It is to be understood that the lens of FIG. 1 can be made as a one piece unit or from other materials. The members 3 may be straight in their thin plans as shown in FIGS. 2 and 4 or maybe vaulted or angulated as shown in FIGS. 3 and 5.

The peripheral haptic design which provides tissue touch and fixation may vary from a broad arc of tissue contact to a two point fixation per loop or a single point of fixation per loop whereby two point, three point, or four point fixation may be achieved for the lens overall. Each of these methods of fixation, two point, three point, four point, and arcuate or any combination thereof has particular design advantages.

Figure 8:
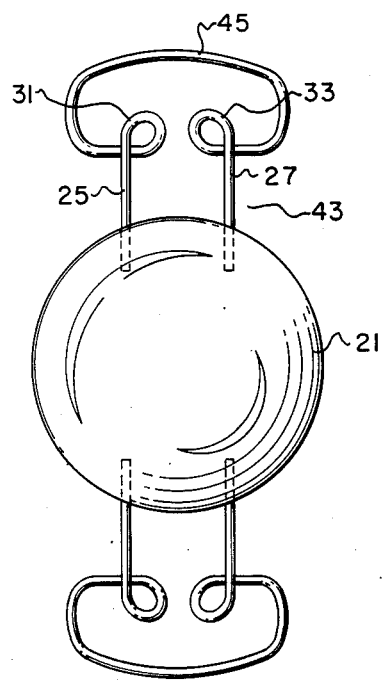
FIG. 8 is an intraocular lens having two closed loop haptics each of which has two coils. The peripheral portions of the haptics are more round than those of FIG. 1.

In FIGS. 8 and 9, the fixation members 23 are the same as those of FIG. 2 except that each of the peripheral portions 45 of the position fixation members 43 has a broad arc thereby providing a broad arc of tissue contact.

Figure 10:
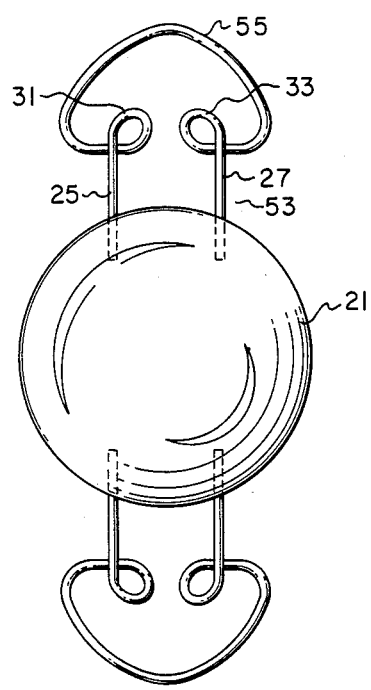
FIG. 10 is an intraocular lens having two closed loop haptics each of which has two coils. The peripheral portions of the haptics are more pointed than those of FIGS. 1 and 8.

In FIG. 10, the position fixation members 53 each have a rounded but more pointed peripheral portion 55 thereby providing one point fixation per loop or a total of two point fixation for the lens overall.

Figure 11:
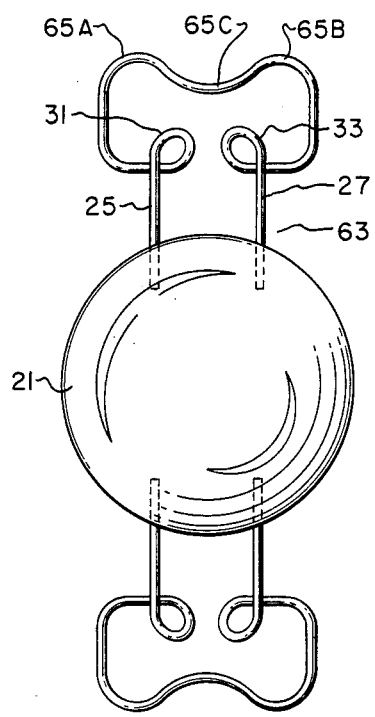
FIG. 11 is an intraocular lens having two closed loop haptics each of which has two coils. The peripheral portions of each of the haptics are shaped to provide two rounded position fixation portions whereby four point fixation is provided for the lens overall.

In FIG. 11, the position fixation members 63 each have two rounded peripheral portions 65A and 65B for engagement of the tissue of the eye with a concave portion 65C there between. This lens provides two point fixation per loop or a total of four point fixation for the lens overall. The peripheral portion 65A–65C of the position fixation members 63 of the lens of FIG. 11 has advantages in that the concave portions 65C may act to minimize over growth of tissue in the periphery of the eye from the iris over the haptic and in addition provides curvature to allow for manipulation of the loop with small instruments during implantation.

Figure 12:
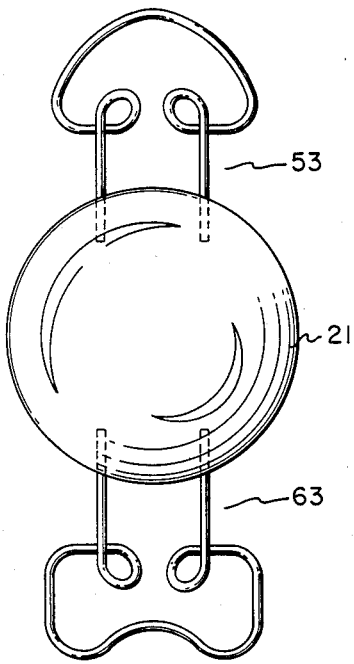
FIG. 12 is an intraocular lens having two closed loop haptics one of which is of the type shown in FIG. 10 and the other of which is of the type shown in FIG. 11.

The lens of FIG. 12 employs one closed loop haptic 53 of the embodiment of FIG. 10 and one closed loop haptic 63 of the embodiment of FIG. 11 whereby the lens overall has a total of three point fixation.

The position fixation members 43, 53 and 63 of the lenses of FIGS. 8–12 all have the coil portion 31 and 33 which act in the same manner as the coil portions 31 and 33 of the lens of FIG. 1 to provide the desired flexibilty to prevent or minimize anterior optic movement, and to provide geometrically stable haptic flexion in closed loop haptics as described in connection with the lens of FIG. 1. In each of these lenses, the coils 31 and 33 open or unwind when pressure is applied to the peripheral portions of their haptics towards the lens body.

The lens of FIG. 17 is including the fixation members 23 is the same as that of FIG. 1 except that the stems 25 and 27 are connected to the lens body 21 at points closer together than as shown in FIG. 1 and then diverge at points 25C and 27C such that the coils 31 and 33 are at a slightly greater distance apart than those of FIG. 1.

The lens of FIG. 8 is intended for use preferably in the anterior chamber of the eye due to its broad axis of its peripheral portions 45 although it could be implanted in the posterior chamber. The lenses of FIGS. 10, 11, 12 and 17 will be preferably implanted in the anterior chamber. The lens of FIGS. 8-12 and 17 can be made such that their optic 21 can be formed from a separate piece of suitable plastic and their fixation members can be formed separately from suitable plastic and then attached to the lens body by inserting their stems into aperatures drilled into the periphery of the lens body and secured by suitable heat treatment.

Figure 13:
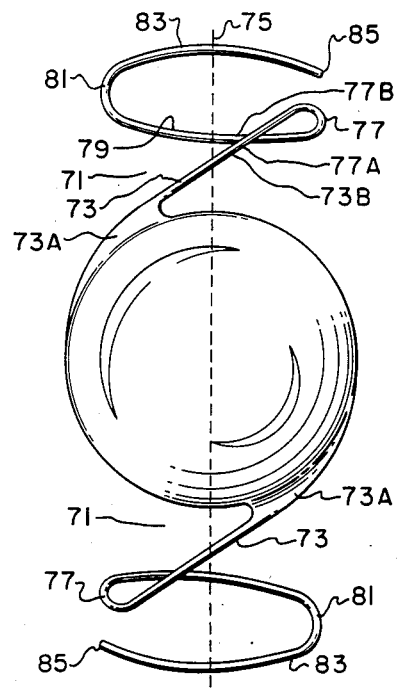
FIG. 13 is an intraocular lens having two open loop haptics each of which has one coil. The peripheral portions of the haptics provide broad arcs of tissue contact.

Referring now to FIG. 13, the lens illustrated therein comprises a transparent central or medial lens body 21 having two open loop position fixation members 71 extending from opposite sides of the periphery of the body 21. The position fixation members 71 are identical in shape but are asyametrically arranged relative to the lens body 21. Each member 71 comprises a proximal arm or stem 73 having an end 73A join proximally to the lens body 21 on one side of a plane 75 coinciding with and passing through the axis of the lens body. The arm 73 crosses the plane 75 where its other end 73B is formed into a coil 77 having ends 77A and 77B which cross each other. The end 77B of the coil 77 extends to an arm portion 79 which crosses the plane 75 and then curves sharply back on itself in a hairpin configuration forming an elbow 81 which then continues in a general broad outwardly convex curve portion 83 which crosses the plane 75 again to a free end 85. Thus the base 73A of the stem and the elbow 81 are on one side of the plane 75 (on the left side as seen in FIG. 13) and the coil 77 and the free end 85 are on the other side of the plane 75 (on the right side as seen in FIG. 13). The components of the other position fixation member 71 are located in reverse positions relative to the plane 75 so that its base 73A and elbow 81 are on the right side of the plane as seen in FIG. 13 and its coil 77 and free end 85 are on the left side of the plane 75 as seen in FIG. 13.

The coils or curls 77 of the fixation members 71 have portions 77B which act as a lever to provide flexibility when compression forces are applied to the fixation members in attempt to shorten the member. This lever-like action causes each coil or curve to unwind, open up or enlarge in its diameter yielding to the force of compression causing the lever arm to move in an arc-like path towards the optic. Each coil or curl consists of the loop member 71 passing under itself (as seen in FIG. 13) as the loop progresses from the optic. That is the loop member 71 begins from its fixed position at the optic, progresses outwardly, begins its curl, completes the curl by passing under itself to then progress further to the elbow and then to the outer portion of the loop. By passing under itself in this fashion without attachment, the lever arm of the loop member 71 is free to follow its arcuate path towards the optic without touching the outer portion of the loop member 71 which might impede or inhibit its movement.

The overall design of the fixation loop members 71 provides flexibility of the arm portions 73 about the base junction 73A, along the stem 73, about the coil 77, at the elbow 81 and along the outward convex portion 83. The lens may be cut and polished from a single piece of plastic material. The intraocular lens of FIG. 13 preferably is to be used in the posterior chamber of the eye although it can be used in the anterior chamber. The design of the fixation members 71 including their coils 77 provide the desired flexibility for use in either the posterior or anterior chambers of the eye and prevent anterior optic movement and provide for geometrically stable haptic flexion.

The intraocular lens of FIG. 14 is the same as that of FIG. 13 except that the stems 73 are curved rather than straight. In addition, the coils 77 of the lens of FIG. 14 are somewhat larger than the coils 77 of the lens of FIG. 13. The intraocular lens of FIGS. 13 and 14 have broad arc shaped peripheral portions 83 for providing a broad area of tissue contact fixation when the lens is implanted in the eye. The lens of FIG. 14 can be implanted in the posterior chamber, however, it can also be implanted in the anterior chamber of the eye.

The intraocular lens of FIG. 15 is the same as that of FIG. 14 except that its peripheral tissuing engaging portions of the fixation members 71 each comprise two rounded tissue contacting portions 91 and 93 with a concave intermediate portion 95. This lens overall provides for four point fixation. The concave portion 95 serves the same purpose as the concave portion 65C of the lens in FIG. 11. The lens of FIG. 15 preferably will be implanted in the anterior chamber of the eye, however, it can be implanted in the posterior chamber. The lens of FIG. 15 has advantage over the lens of FIGS. 13 and 14 in that there is reduced tissue touch.

The intraocular lens of FIG. 16 is similar to that of FIG. 14 except that the peripheral tissue engaging portions of the fixation members 71 each having three rounded tissue engaging portions 101, 102 and 103 with a concave portion 104 between rounded portions 101 and 102 and a concave portion 105 between rounded portions 102 and 103. This lens provides for six point fixation overall and has advantage over the lens in FIG. 15 in that it has more areas of touch which begin to approximate the broad area of touch of the arc of the lenses of FIGS. 13 and 14 yet there is not as much tissue touch. The concave portions 104 and 105 act to minimize or prevent the over growth of tissue in the periphery of the eye from the iris over the haptic. They also allow for manipulation of the lens with small instruments. The intraocular lens of FIG. 16 preferably will be used in the anterior chamber of the eye.

Preferably the lens of FIG. 14-16 each will be cut and polished from a single piece of suitable plastic material.

Figure 18:
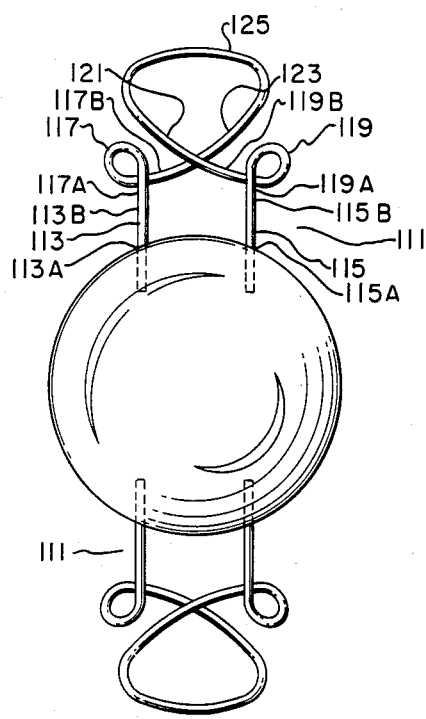
FIG. 18 is an intraocular lens having two closed loop haptics each of which has two coils located on the outside of the stems.

Referring to FIG. 18, the lens comprises a lens body 21 having two closed loop haptics or position fixation members 111. Each member 111 comprises two stems 113 and 115 having ends 113A and 115A joined to the periphery of the lens body 21. The other ends 113B and 115B of the stems are formed into coils or curls 117 and 119 having ends 117A, 117B and 119A, 119B which cross each other. The ends 117B and 119B extend to arm portions 121 and 123 which cross each other and which in turn extend to a peripheral or seating portion 125 adapted to seat against or engage the tissue of the eye. The coils 117 and 119 act in the same manner as coils 31 and 33 of the lenses having closed loop haptics as previously described in that they provide flexibility and geometric stable haptic flexion thereby preventing anterior optic movement when pressure is applied to the peripheral portions 125 towards the lens body 21. The coils 117 and 119 unwind or open when compression forces are applied to the peripheral portions 125 tending to shorten the fixation members 111. The lens body 21 and the fixation members 111 can be formed of suitable plastic material. The lens of FIG. 18 preferably will be implanted in the posterior chamber of the eye although it could be used in the anterior chamber.

Figure 19:
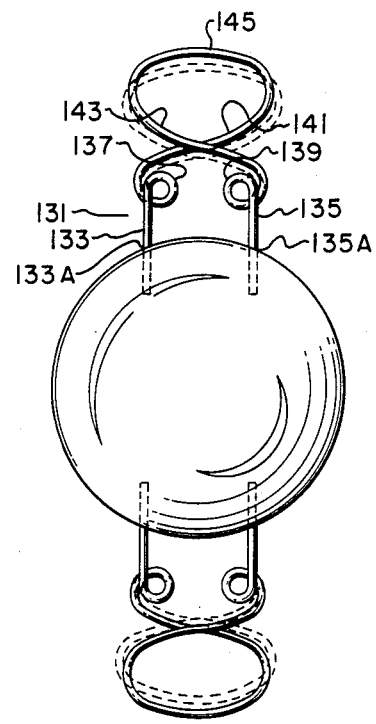
FIG. 19 is an intraocular lens having two closed loop haptics each of which has two coils formed to wind or close when pressure is applied to the peripheral portion towards the lens body. The dotted lines illustrate positions to which the haptics move when pressure is applied to the haptics toward the lens body.

Referring to FIG. 19, the intraocular lens comprises a an optic of lens body 21 having two closed loop haptic of fixation position members 131 which are identical to each other. Each member 131 comprises two stems 133 and 135 having ends 133A and 135A which are joined to the periphery of the lens body 121, for example, by being inserted into aperatures formed into the periphery of the lens body and secured therein by suitable heat treatment. The other ends of the stems 133 are formed into coils or curls 137 and 139 having ends which cross each other respectively. The coils 137 and 139 then extend to arm portions 141 and 143 which cross each other and then extend to a peripheral or seating portion 145 adapted to seat against or engage the tissue of the eye. The coils 137 and 139 provide the desired flexibility and yet allow for geometrically stable haptic flexion on the application of compression forces to the peripheral portions 145 towards the lens body. When compression forces are applied to the peripheral portions 145 of the members 131 towards the lens body, the coils 137 and 139 tend to wind or close rather than unwind or open as occurred in the operation of the haptics of the lenses described previously. The closure or winding of the coils 137 and 139 not only has the advantage of preventing of minimizing anterior optic movement but tends to draw the optic back away from the cornea.

In the lens of FIG. 18, the coils 117 and 119 are located on the outside of the stems 113 and 115. In the lens of FIG. 19, the coils 137 and 139 are located on the inside of the stems 133 and 135.

Figure 20:
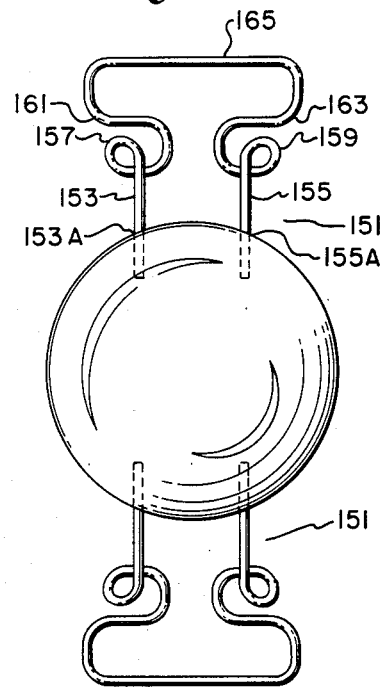
FIG. 20 is an intraocular lens having two closed loop haptics each of which has two coils formed to wind or close when pressure is applied to the peripheral portion towards the lens body. The coils of each haptic are located on the outside of the stems.

Referring to FIG. 20, the intraocular lens comprises an optic or lens body 21 having two closed loop haptics or fixation position members 151 which are identical to each other. Each member 151 comprises two stems 153 and 155 having ends 153A and 155A which are joined to the periphery of the lens body 21 periphery, for example, by being inserted into aperatures formed into the periphery of the lens body and secured therein by suitable heat treatment. The other ends of the stems 153 and 155 are formed into coils or curls 157 and 159 having ends which cross each other respectively. The coils then extend to arm portions 161 and 163 which extend from the coils inwardly and outwardly and then extend to a peripheral seating portion 165 adapted to seat against or engage the tissue of the eye. The coils 157 and 159 provide the desired flexibility and yet result in geometrically stable haptic flexion upon the application of the compression forces to the peripheral portions 165 of the members 151 towards the lens body. When compressive force is applied to the peripheral portions 165 of the members 151 towards the lens body, the coils 157 and 159 tend to wind or close. Closure or winding of the coils 157 and 159 not only have the advantage of preventing or minimizing anterior optic movement but also tend to draw the optic backward from the cornea assuming that the optic is located in the anterior chamber of the eye.

Figure 21:
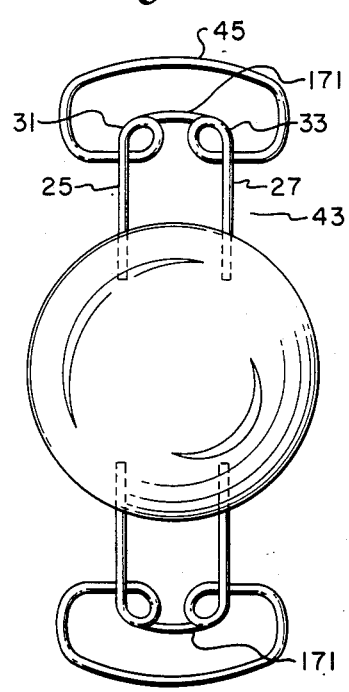
FIG. 21 is an intraocular lens similar to that of FIG. 1 but with connecting portions coupled between the coils of each haptic.

Referring to FIG. 21, the intraocular lens shown is the same as that illustrated in FIG. 8 except that connecting portions 171 are connected between the coils 31 and 33 at portions closest to the peripheral portion 45. The connecting portions 171 do not interfere with the opening or unwinding of the coils upon the application of pressure to the peripheral portions 45 towards the lens body but do prevent the stems 25 and 27 from moving away or moving toward each other upon the application of this pressure. Similar connecting portions may be connected in the same manner to the coils of the lenses of FIGS. 1, 10, 11, 12 and 17.

The optic of all of the lenses of FIGS. 1 and 8-21 may be of the convex planar shape as shown in FIGS. 2 and 3, of the biconvex shape as shown in FIGS. 4 and 5 or of other suitable configurations. In addition, the haptics of the intraocular lens of FIGS. 1 and 8-21 whether in the form of a closed loop haptic or an open loop haptic or a combination thereof may be straight as shown in FIGS. 2 and 4 or angulated or vaulted as shown in FIGS. 3 and 5. Vaulting is desirable for lenses that are to be located in the anterior chamber of the eye to locate the lens body or optic anterior or forward of the iris as disclosed in U.S. Pat. No. 4,418,431. Vaulting also is desirable for lenses in the posterior chamber. It keeps the lens away from the iris and also nearer to the theoretically desirable nodal point. For the lenses that have angulated or vaulted haptics, the coil portions of the coils leading to the peripheral seating portions of the haptics will curl or coil behind the coil portion that extends to the stems, for example, as shown in FIGS. 2 and 5. In this application, the term behind, means that the coil portion which extends to the peripheral seating portion of the haptic will be closer to the plane of the peripheral portion of the haptic than the portion of the coil that extends to the stem. The purpose of this arrangement is to prevent the coil from bumping into the stem during flexion which may occur, for example, if the coil portion which extends to the peripheral seating portion of the haptic is forward of the portion of the coil connected to the stem in a vaulted or angulated haptic.

Although the intraocular lenses shown either have two closed loop haptics or two open loop haptics, it is to be understood that one of the open loop haptics of the invention could be employed in a lens with one of the closed loop haptics of the invention depending upon the design desired. In addition, one of the open loop haptics of the invention could be employed in a lens with a different type of haptic or one of the closed loop haptics of the invention could be employed in a lens with a different type of haptic.

I claim:

1. An intraocular lens suitable for use as an artificial lens implant in the human eye, comprising:

a lens body having first and second position fixation members extending from opposite sides of the periphery of said lens body, each of said position fixation members comprising a stem portion having first and second ends, a coil portion having first and second ends, and a peripheral portion extending to a position such that it may engage the tissue of the eye, each of said coil portions being located between said lens body and the peripheral portion of its position fixation member, said first end of each of said stem portions being joined to said lens body, said second end of each of said stem portions being joined to said first end of its associated coil portion, said first and second ends of each of said coil portions cross each other as seen in a plane generally perpendicular to the axis to said lens body, each of said second ends of each of said coil portions being coupled to the peripheral portion of its position fixation member by way of a transverse portion which is generally transverse to a second plane coinciding with and passing through the axis of said lens body and through said peripheral portions of said first and second position fixation members such that when pressure is applied to said peripheral portions of said position fixation members towards said lens body, pressure is applied to said coil portions by way of said transverse portions to provide for flexibility of said position fixation members.

2. The intraocular lens of claim 1, wherein:
each of said coil portions of each of said first and second fixation position members is formed such that it will tend to unwind and open upon the application of pressure to its associated peripheral portion, towards said lens body.

3. The intraocular lens of claim 1, wherein:
each of said coil portions of said first and second fixation position members is formed such that it will tend to wind and close upon the application of pressure to its associated peripheral portion, towards said lens body.

4. The intraocular lens of claims 1, 2, or 3, wherein:
the opening of each of said coil portions faces in a direction generally parallel to the axis of said lens body.

5. The intraocular lens of claim 1, wherein:
said peripheral portion of each of said position fixation members has a free end.

6. The intraocular lens of claim 2, wherein:
said peripheral portion of each of said fixation position members has a free end.

7. The intraocular lens of claim 1, wherein:
each of said position fixation members comprises an elbow joining a first end of its peripheral portion to said second end of its coil portion with the opposite end of its peripheral portion comprising a free end, the positions where said stem portions of said first and second position fixation members join said lens body being located on opposite sides of said second plane,
each of said position fixation members having its elbow and the position where its stem portion joins said lens body, located on the same side of said second plane opposite the side on which its free end and its coil portion are located.

8. The intraocular lens of claim 7, wherein:
the opening of each of said coil portions of said first and second portion fixation members faces in a direction generally parallel to the axis of said lens body.

9. The intraocular lens of claim 8, wherein:
each of said coil portions of said first and second position fixation members is formed such that it will tend to unwind and open upon the application of pressure to its associated peripheral portion, towards said lens body.

10. The intraocular lens of claims 1, where each of said first and second position fixation members comprises:
first and second stem portions each having first and second ends and first and second coil portions each having first and second ends,
said first ends of said first and second stem portions being joined to said lens body at spaced apart positions,
said second ends of said first and second stem portions being joined to said first ends of said first and scond coil portions respectively, and
said second ends of said first and second coil portions being coupled to opposite ends of its associated peripheral portion.

11. The intraocular lens of claim 10, wherein:
each of said coil portions of first and second position fixation members is formed such that it will tend to unwind and open upon the application of pressure to its associated peripheral portion, towards said lens body.

12. The intraocular lens of claim 10, wherein:
each of said coil portions of said first and second position fixation members is formed such that it will tend to wind and close upon the application of pressure to its associated peripheral portion, towards said lens body.

13. The intraocular lens of claims 10, 11, or 12, wherein:
the opening of each of said coil portions of said first and second position fixation members faces in a direction generally parallel to the axis of said lens body.

14. An intraocular lens suitable for use as an aritifical lens implant in the human eye, comprising:
a lens body having a position fixation member extending from a side of said lens body,
said position fixation member comprising a stem portion having first and second ends, a coil portion having first and second ends, an elbow, and a peripheral portion extending to a position such that it may engage the tissue of the eye,
said first end of said stem portion being joined to said lens body,
said second end of said stem portion being joined to said first end of said coil portion,
said first and second ends of said coil portion cross each other as seen in a plane generally perpendicular to the axis of said lens body,
said elbow joining a first end of said peripheral portion to said second end of said coil portion with the opposite end of said peripheral portion comprising a free end,
the position where said first end of said stem of said position fixation member joins said lens body and said elbow being located on a first side of a second plane coinciding with and passing through the axis of said lens body and through said peripheral portion,
the free end of said peripheral portion of said position fixation member and at least a portion of said coil portion being located on a second side of said second plane which is opposite to said first side.
said fixation position member being flexible at least about said coil portion when pressure is applied to said peripheral portion towards said lens body.

15. The intraocular lens of claim 14, wherein:
said coil portion is formed such that it will tend to unwind and open when pressure is applied to said peripheral portion towards said lens body.

16. The intraocular lens of claim 14, wherein:
said coil portion, from its first end comprises an outer portion that extends away from said second plane, a portion that extends toward said lens body, and an inner portion that extends toward said second plane to its second end,
said inner portion being located between said outer portion and said lens body such that said coil portion will tend to unwind and open when pressure is applied to said peripheral portion towards said lens body.

17. An intraocular lens suitable for use as an artificial lens implant in the human eye, comprising:
a lens body having a position fixation member extending from a side of said lens body, said position fixation member comprising first and second stem portions each having first and second ends, first and second coil portions each having first and second ends, and a peripheral portion, said first ends of said first and second stem portions being joined to said lens body at spaced apart positions, said first and second ends of each of said coil portions cross each other as seen in a plane generally perpendicular to the axis of said lens body, said second ends of said first and second stem portions being joined to said first ends of said first and second coil portions, respectively, said second ends of first and second coil portions being joined to opposite ends of said peripheral portion such that said peripheral portion extends to a position such that it may engage the tissue of the eye, said position fixation member being flexible about said first and second coil portions when pressure is applied to said peripheral portion towards said lens body.

18. The intraocular lens of claim 17, wherein:
each of said second ends of each of said coil portions is coupled to said peripheral portion by way of a transverse portion which is generally transverse to a plane coinciding with and passing through the axis of said lens body and through said peripheral portion.

19. The intraocular lens of claim 17, wherein:
said first and second coil portions are located between said peripheral portion and the nearest edge of said lens body.

20. The intraocular lens of claim 17, wherein:
said first and second coil portions are formed such that they will tend to unwind and open upon the application of force to said peripheral portions towards said lens body.

21. The intraocular lens of claim 17, wherein:
said first and second coil portions are formed such that they will tend to wind and close upon the application of force to said peripheral portion towards said lens body.

22. The intraocular lens of claim 17 wherein:
said first stem portion and said first coil portion are located on a first side of a second plane passing through the axis of said lens body and through said peripheral portion,
said second stem portion and said second coil portion are located on a side of said second plane opposite said first side,
each of said coil portions, from its first end comprises an outer portion that extends toward said second plane, a portion that extends toward said lens body, and an inner portion that extends away from said second plane to its second end,
said first coil portion having its second end joined to said peripheral portion on the same side of said second plane on which first coil portion is located,
said second coil portion having its second end joined to said peripheral portion on the same side of said second plane on which said second coil portion is located,
said inner portion of each of said coil portions being located between its outer portion and said lens body such that said first and second coil portions will tend to unwind and open when pressure is applied to said peripheral portion towards said lens body.

23. The intraocular lens of claim 22 wherein said second end of each of said coil portions is joined to said peripheral portion by a transverse portion which is generally transverse to said second plane and which acts as a lever arm to cause its coil portion to unwind and open when pressure is applied to said peripheral portion toward said lens body.

24. The intraocular lens of claim 17, wherein:
said first stem portion and said first coil portion are located on a first side of a second plane passing through the axis of said lens body and through said peripheral portion,
said second stem portion and said second coil portion are located on a side of said second plane opposite said first side,
each of said coil portions, from its first end comprises an outer portion that extends away from said second plane, a portion that extends toward said lens body, and an inner portion that extends toward said second plane to is second end,
a first intermediate portion extends from said second end of said first coil portion through said second plane to one end of said peripheral portion,
a second intermediate portion extends from said second end of said second coil portion through said second plane to the other end of said peripheral portion,
said first and second intermediate portions cross each other as seen in said plane generally perpendicular to the axis of said lens body,
said inner portion of each of said coil portions being located between its outer portion and said lens body such that said first and second coil portions will tend to unwind and open when pressure is applied to said peripheral portion towards said lens body.

25. The intraocular lens of claim 17, wherein:
said first stem portion and said first coil portion are located on a first side of a second plane passing through the axis of said lens body and through said peripheral portion,
said second stem position and said second coil portion are located on a side of said second plane opposite said first side,
each of said coil portions, from its first end comprises an outer portion that extends toward said second plane, a portion that extends toward said lens body, and an inner portion that extends away from said second plane to its second end,
a first intermediate portion extends from said second end of said first coil portion through said second plane to one end of said peripheral portion,
a second intermediate portion extends from said second end of said second coil portion through said second plane to the other end of said peripheral portion,
said first and second intermediate portions cross each other as seen in said plane generally perpendicular to the axis of said lens body,
said first and second coil portions being located between said first and second intermediate portions respectively and said lens body such that said first and second coil portions will tend to wind and close when pressure is applied to said peripheral portion towards said lens body.

26. The intraocular lens of claim 17, wherein:
said first stem portion and said first coil portion are located on a first side of a second plane passing through the axis of said lens body and through said peripheral portion, said second stem portion and said second coil portion are located on a side of said second plane opposite said first side, each of said coil portions from its first end comprises a first outer portion that extends away from said second plane, a portion that extends toward said lens body, an inner portion that extends toward said second plane, a portion that extends away from said lens body, and a second outer portion that extends away from said second plane and then to one end of said peripheral portion on the same side of said second plane that its coil is located, each of said first and second coil portions being located between its second outer portion and said lens body such that said first and second coil portions will tend to wind and close when pressure is applied to said peripheral portion toward said lens body.

* * * * *